(12) United States Patent
Zicker et al.

(10) Patent No.: US 8,841,344 B2
(45) Date of Patent: Sep. 23, 2014

(54) METHOD OF USING OMEGA-3 FATTY ACIDS

(75) Inventors: Steven Curtis Zicker, Lawrence, KS (US); Chadwick E. Dodd, Lawrence, KS (US); Dennis Jewell, Perry, KS (US); Dale A. Fritsch, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1519 days.

(21) Appl. No.: 10/065,326

(22) Filed: Oct. 3, 2002

(65) Prior Publication Data

US 2004/0068010 A1   Apr. 8, 2004

(51) Int. Cl.
*A61K 31/20* (2006.01)
*A61K 31/202* (2006.01)

(52) U.S. Cl.
CPC .................................. *A61K 31/202* (2013.01)
USPC ........................................................ 514/560

(58) Field of Classification Search
CPC ................................................... A61K 31/202
USPC .................................................. 514/558, 560
See application file for complete search history.

(56) References Cited

U.S. PATENT DOCUMENTS

| | | | |
|---|---|---|---|
| 5,776,913 | A | 7/1998 | Ogilvie et al. |
| 6,015,798 | A | 1/2000 | Ogilvie et al. |
| 6,297,280 | B1 | 10/2001 | Ishihara et al. |
| 2003/0194478 | A1 | 10/2003 | Davenport et al. |
| 2004/0068010 | A1 | 4/2004 | Zicker et al. |

FOREIGN PATENT DOCUMENTS

| | | | |
|---|---|---|---|
| EP | | 0678247 A1 * | 10/1995 |
| WO | WO 2004/006688 A1 * | | 1/2004 |

OTHER PUBLICATIONS

Reisbick et al. Omega-3 Fatty Acid Deficiency and Behavior: A cirtical review and directions for future research. Handbook of Essential Fatty Acid Biology: Biochemistry, Physiology and Behavior Neurobiology: Chapter 17 pp. 397-426.*
Borras D, et al., "Age related changes in the brain of the dog", Vet Pathol 36:202-211;1999.
Brigelius-Flohe R, et al., "Vitamin E: function and metabolism", FASEB J 13:1155; 1999.
Cao G, et al., "Increases in human plasma antioxidant capacity after consumption of controlled diets high in fruit and vegetables", Am J Clin Nutr 68:1081-1087;1998.
Cummings BJ, Head E, Ruehl W, Milgram NW, Cotman CW. The canine as an animal model of human aging and dementia. Neurobiology of Aging, 17:259-268:1996.
Frei B. "Molecular and biological mechanisms of antioxidant action", FASEB J 13:963-964;1999.
Fujimoto K., et al., "The effect of dietary docosahexaenoate on the learning ability of rats", Health Effects of Fish and Fish Oils, St. John's Newfoundland: ARTS Biomedical Publishers and Distributors, 1989; 275-284.
Hagen TM., et al., "(R)-α-Lipoic acid-supplemented old rats have improved mitochondrial function, decreased oxidative damage, and increased metabolic rate", FASEB J 13:411-418;1999.
Harman D. Free radical theory of aging: a hypothesis on pathogenesis of senile dementia of the Alzheimer's type. Age 16:23-30;1993.
Head, E, Cotman CW. Milgram NW, Ruehl WW. Spatial learning and memory as a function of age in the dog. Behavioral Neuroscience 109:851-858;1995.
Jones CR, Arai T, Rapoport SI, Evidence of the involvement of docosahexaenoic acid in cholinergic stimulated signal transduction at the synapse. Neurochemical Research 1997; 22:663-670.
Leveque NW. Cognitive dysfunction in dogs, cats an Alzheimer's-like disease. J AM Vet Med Assoc 212:1351; 1998.
Lovell MA, Ehmann WD, Mattson, MP, Markesbery WR, Elevated 4-hydroxynonenal in ventricular fluid in Alzheimer's disease. Neurobiology of Aging 18:457-461;1997.
Markesbery WR, Lovell MA. Four-hydroxynonenal, a product of lipid peroxidation, is increased in the brain in Alzheimer's disease. Neurobiology of Aging 19:33-36;1998.
McGahon BM, Murray CA, Horrobin DF, Lynch MA. Age-related changes in oxidative mechanisms and LTP are reversed by dietary manipulation. Neurobiology of Aging 1999: 20:643-653.
McGahon BM, Martin DSD, Horrobin DF, Lynch MA. Age-related changes in synaptic function: analysis of the effect of dietary supplementation with omega-3 fatty acids. Neuroscience 1999; 94:305-314.
Milgram NW, et al., "Landmark discrimination learning in the dog", Learning & Memory, 6:54-61;1999.
Milgram NW, Head E, Weiner E, Thomas E. Cognitive functions and aging in the dog: acquisition of nonspatial visual tasks. Behavioral Neuroscience 108:57-68;1994.
Rogers PJ., "A healthy body, a healthy mind: long-term impact of diet on mood and cognitive function", Proceedings of the Nutrition Society 2001; 60:135-143.
Sano M, Ernesto C, Thomas, RG, et al. A controlled trial of selegilene, alpha-tocopherol, or both as treatment for Alzheimer's disease. New England Journal of Medicine 336:1216-1222;1997.
Schoenherr WD, Jewell DE. Nutritional modification of inflammatory diseases. Seminars in Veterinary Medicine and Surgery (Small Animal) 1997; 12:212-222.
Weaver BJ, Holub BJ. Health effects and metabolism of dietary eicosapentaenoic acid. Prog Food Nutr Sci 1988; 12:111-150.

(Continued)

*Primary Examiner* — Jennifer M Kim
(74) *Attorney, Agent, or Firm* — Thomas M. Hunter

(57) ABSTRACT

A method for influencing behavior in young, adult or aged pet animals which comprises systemically administering a behavior influencing quantity of an omega-3 fatty acid or mixture of omega-3 fatty acids.

8 Claims, No Drawings

(56) References Cited

OTHER PUBLICATIONS

Youdim KA, Martin A, Joseph JA. Essential fatty acids and the brain: possible health implications. Int J. Devl Neurosciences 2000; 18: 383-399.

Ahlstrom et al., 2004, "Fatty Acid composition in commercial dog foods," J. Nutrition 134(8 Suppl):2145S-2147S.

Bain et al., 2001, "Predicting behavioral changes associated with age-related cognitive impairment in dogs," J. Amer. Vet. Med. Assoc. 218(11):1792-1795.

Dodd et al., 2002, "Effect of an Investigational Food on Age-Related Behavioral Changes in Dogs," Hill's European Symposium on Canine Brain Ageing, Barcelona, Spain.

Dodd et al., 2003, "Can a fortified food affect the behavioral manifestations of age-related cognitive decline in dogs?" Vet. Med. 98:396-408.

Hand, ed., 2000, Small Animal Clinical Nutrition, Chapter 13, pp. 127-146, 402-430.

Landsberg et al., 2005, "Behavior problems in geriatric pets," Vet. Clin. North Amer. Small Animal Practice 35(3):675-698.

Neilson et al., 2001, "Prevalence of behavioral changes associated with age-related cognitive impairment in dogs," J. Amer. Vet. Med. Assoc. 218(11):1787-1791.

Ruehl et al., 1995, "Canine cognitive dysfunction as a model for human age-related cognitive decline, dementia and Alzheimer's disease: clinical presentation, cognitive testing, pathology and response to 1-deprenyl therapy," Prog. Brain Research 106:217-225.

* cited by examiner

METHOD OF USING OMEGA-3 FATTY ACIDS

BACKGROUND OF INVENTION

Omega-3-fatty acids are known to be beneficial to mammals. Some of their benefits are disclosed in U.S. Pat. No. 5,776,913 wherein specific diets can ameliorate metabolic disturbances in animals with cancer. Omega-3-fatty acids are typically, exemplified by eicosapentaenoic acid (EPA) and docosahexaenoic (DHA), a-linolenic acid, and octadecatetraenoic acid. EPA and DHA are generally considered to be the most important and significant of the long chain omega-3 fatty acids. Generally, these long chain fatty acids are present in relatively low, almost minute, quantities or completely absent in typical pet food compositions. The fatty acid composition of foods consumed by companion pets, for example dogs and cats, directly influences the biological levels of fatty acid found in their blood.

Natural products which have relatively high levels of omega-3 unsaturated fatty acids such as EPA and DHA can be derived from marine oils such as salmon, anchovy, sardine and menhaden. Such natural oils can be concentrated to even higher percentages of omega-3-fatty acids.

When provided systemically to pet animals such as dogs and cats in the proper quantities, omega-3 fatty acids can assist in and positively influence behavior in young, adult and aged animals. Such behavior influences can be particularly important in animals having age related cognition decline (ARCD). However, even in young and mature animals that are not of an age wherein ARCD is normally found, the systemic administration of omega-3 fatty acids can bring about positive behavior changes.

SUMMARY OF INVENTION

In accordance with the invention there is a method for influencing behavior in adult or aged pet animals which comprises systemically administering a behavior influencing quantity of an omega-3 fatty acid or mixture of omega-3 fatty acids.

A further aspect of the invention is a composition suitable for oral ingestion by an adult or aged pet animal comprising a carrier and a behavior influencing quantity of an omega-3 fatty acid or mixture of omega-3 fatty acids.

DETAILED DESCRIPTION

Omega-3-fatty acids are a recognized group of polyunsaturated fatty carboxylic acids. They have long chain polyalkenyl groups, which are normal or branched, with about 8 to about 24 carbon atoms, preferably about 10 to about 22 carbon atoms, including the carbon atom of the carboxyl group. These are acids which have a double bond between the 3 and 4 carbon atoms as measured from the end of the molecule not containing the carboxy group. Chief among the omega-3-fatty acids is the aforementioned EPA and DHA fatty acids. Derivatives of omega-3 fatty acids can also be employed. Many types of derivatives are well known to one skilled in the art. Examples of suitable derivatives are esters, such as branched or unbranched and/or saturated or unsaturated $C_1$-$C_{30}$ cycloalkyl esters, in particular $C_1$-$C_6$ alkyl esters. Their systemic potential has been recognized in the art, for example U.S. Pat. Nos. 5,776,913 and 6,015,798. As used in this application and claims "omega-3 fatty acid" includes its derivatives.

With respect to the quantity of the omega-3 fatty acid or mixture of omega-3 fatty acids, a minimum amount of about 0.5 wt. %, preferably above about 1.0 wt. %, or 2 wt. %, on a dry matter basis, as measured by quantity of daily diet composition should be administered. Generally no more than about 10 wt. %, preferably no more than about 7, 5, or 4 wt. % can be employed. EPA and DHA are the preferred omega-3 fatty acids. The fatty acids can be administered in a diet such as canned (wet) or dry, in combination with a supplement such as a treat in liquid or solid form, or in the water supply or even as a separate dosage unit, for example a capsule or tablet containing the omega-3 fatty acid or mixture of omega-3 fatty acids.

The omega-3 fatty acid or mixture thereof is systemically administered to a pet cat or dog preferably having observable decline in established behavior practices. However, it can be administered to a pet animal not having an observable behavior decline in established behavior practices and one can see a positive change in behavior practices. A young cat or dog is up to about 1 year of age. An adult animal, cat or dog, is generally from about 1 to 6 years of age while an aged cat or dog is about 7 years of age or older. Preferably, pet animals having at least one of cancer, and/or arthritis can be excluded from treatment.

Examples of behavior which can be altered for the positive by the systemic administration of omega-3 fatty acids include memory; learning; disorientation including at least one of awareness of surroundings, circling, aimless activity, inappropriate vocalization; interactions including at least one of family recognition, animal recognition, family interaction, animal interaction, greeting enthusiasm, attention seeking, response to verbal commands; activity such as agility and level of activity; irregular sleep pattern; housetraining; and any behavior associated with ARCD.

Improvement in at least one of these areas can be observed in pets even though there may not be an observable loss in behavioral function. It is preferable to systemically provide the active omega-3 fatty acid(s) when a loss in capacity has been observed. Generally an improvement in the behavior is observed after one to two weeks of omega-3 administration, although sometimes it can take several months, up to about six months for a positive change in behavior.

Below is an example of a specific diet, which can be used to supply the omega-3 fatty acid or mixture thereof:

| Canine Adult Maintenance Diet Wt. % as Dry Matter | |
| --- | --- |
| Protein | 15-23 |
| Fat | 7-15 |
| Carbohydrate | 40-60 |
| EPA/DHA | 1-5 |

The effect of omega-3 fatty acids can be enhanced by adding other nutrients such as antioxidants, tryptophan, drugs such as SRRI's, and the like.

The invention claimed is:

1. A method for influencing behavior in a dog or cat in need thereof, the method comprising systemically administering to the dog or cat a daily diet comprising at least about 2% by weight of an omega-3 fatty acid or mixture of omega-3 fatty acids selected from the group consisting of eicosapentaenoic acid and docosahexaenoic acid, as measured on a dry matter basis.

2. The method in accordance with claim 1 wherein the dog or cat is about 1 to 6 years of age.

3. The method in accordance with claim 1 wherein the dog or cat is at least about 7 years of age.

4. The method in accordance with claim 1 wherein the dog or cat has an observable behavior deficit prior to administration of the omega-3 fatty acid or mixture thereof.

5. The method in accordance with claim 1 wherein the dog or cat does not have cancer or arthritis.

6. The method in accordance with claim 1 wherein the dog or cat is up to about 1 year of age.

7. The method in accordance with claim 1, wherein the composition comprises no more than about 10% by weight of an omega-3 fatty acid or mixture of omega-3 fatty acids.

8. The method in accordance with claim 7, wherein the composition comprises no more than about 5% by weight of a mixture of EPA and DHA.

* * * * *